United States Patent [19]

Barberet et al.

[11] Patent Number: Plant 5,628

[45] Date of Patent: Jan. 7, 1986

[54] CARNATION NAMED LONGORIN

[76] Inventors: Nicole Barberet, 136 Bld. Kennedy 06 601; Yves Ducloux, Chemin des Ondes 06 601, both of Antibes, France

[21] Appl. No.: 516,568

[22] Filed: Jul. 25, 1983

[51] Int. Cl.[4] ..... A01G 5/00

[52] U.S. Cl. ..... Plt./70

[58] Field of Search ..... Plt./70

*Primary Examiner*—Robert E. Bagwill

[57] ABSTRACT

A new and distinct spray carnation cultivar particularly distinguished by its blossoms the petals of which are a variegation of Shrimp Red and Turkey Red colors, the flowers being borne in a spray on rather rigid, upright stems having abundant foliage, and the plant having a vigorous and upright growth habit which is resistant to *Fusarium oxysporum.*

1 Drawing Figure

BACKGROUND OF THE NEW PLANT

Our new spray carnation cultivar is the result of breeding efforts carried on by us at La Londe, Les Maures, France, since 1975 with the object of developing new spray carnations having nice color, good quality of flower stem and plant growth, and resistance to *Fusarium oxysporum.* This new plant originated as a seedling produced by our crossing of selected and individually identified plants growing among our stock of spray carnations maintained at La Londe for breeding purposes and this particular seedling was selected by us for propagation and test because of its very strong flower coloration and its apparently very favorable growth habit. This discovery plant was reproduced by us at La Londe, by means of cuttings, with such a favorable result with respect to retention by the novel characteristics of the parent plant that we continued such propagation through several successive generations over a period of years, which demonstrated that the novel and distinctive characteristics of the discovery plant are fully retained from generation to generation and appear to be firmly fixed.

DESCRIPTION OF THE DRAWING

Our new spray carnation is illustrated by the accompanying photographic drawing which shows, in full color, the upper portion of a typical flowering stem with buds and flowers in various stages of opening, the colors shown being as nearly true to those specified herein as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—"Fashion" (unpatented).

*Pollen parent.*—Stock Plant No. 72 M C 1. The unnamed variety is individually identified in our permanent records and it, as well as the named variety, is maintained in our carnation collection for breeding purposes at La Londe, France.

Classification:

*Botanic.*—*Dianthus caryophyllus.*

*Commercial.*—Spray Carnation.

Form: Tall, erect bush with at least four stems emitted near the ground.

Height: Averages about 102 cm. at eight months.

Main stem:

*Length.*—Less than 15 cm. due to pinching.

Branching character: Moderately branched.

Growth habit: Vigorous, upright and rigid.

Foliage:

*Quantity.*—Rather abundant.

*Number of leaves.*—At least 120.

*Leaf size.*—Medium, averaging about 10 cm. long and 1 cm. wide at the seventh node.

*Leaf shape.*—Linear with acuminate tip and rolled margins.

*Texture.*—Leathery.

*Color.*—Upper side — 189B. Under side — 189B.

*Ribs and veins.*—Hardly noticeable.

*Rachis.*—Hardly noticeable.

THE BUD

Form: Ovoid.

Size: Medium.

*Diameter.*—About 1.3 cm. in average.

*Length.*—About 3 cm. in average.

Rate of opening: Normal for carnations.

Color of petals:

*When sepals first divide.*—Salmom and Delft Rose.

*When petals begin to unfurl.*—Shrimp Red with Turkey Red variegation.

Sepals:

*Number.*—Five.

*Shape.*—Sepals are joined at the lower part with the upper part of acute form and sharply pointed at the apex. The sepals are hooded over the bud and stand up when the flower opens.

*Color.*—Inside — Greenish White. Outside — 138A.

Calyx:

*Shape.*—Rather cylindrical to bell-shaped.

*Splitting.*—The calyx does not split.

*Aspect.*—Smooth.

Flower stem:

*Length.*—About 62 cm.
*Character.*—Erect and rather thin.
*Color.*—189B.

THE FLOWER

Blooming habit: Recurrent, blooming profusely during the midseason of Spring and Fall.
Size of bloom: Small.
*Diameter.*—Averages about 5.5 cm.
*Depth.*—Averages about 5.2 cm.
Borne: In cluster.
Shape:
*When bloom first opens.*—High centered.
*When bloom matures.*—Dome-shaped.
Petalage:
*Number of petals.*—About 21 in average.
*Arrangement.*—Imbricated.
*Form.*—Fan-shaped, flat at center with undulate margins.
*Texture.*—Soft.
*Color.*—Outer Petal: Body — 33D with 46C margins and body splotches. Base — Greenish yellow. Reverse side — 27A and 46D. Inside Petal: Body — 33D and 46C. Base — Greenish yellow. Reverse side — 27A and 46D.
Flower stem:
*Length.*—About 62 cm. (cut at tenth node).
*Character.*—Upright and of good strength.
*Color.*—189B.
Fragrance: Lightly perceptible.
Persistence: The flower petals hang on and dry.

Lasting quality:
*As cut flower.*—At least ten days in vase keeping.
Disease resistance: Resistant to *Fusarium oxysporum* as observed INRA, Antibes, Alpes-Maritimes, France.

REPRODUCTIVE ORGANS

Stamens:
*Number.*—Ten, in average.
*Arrangement.*—Around the pistils.
*Anthers.*—Size: Less than 4 mm. Color: Whitish.
*Filaments.*—Color — Whitish.
Pistils:
*Number.*—Two.
*Styles.*—Color — Whitish.
*Stigmas.*—Color — Slightly pinkish.
Character of ovaries: Hardly ribbed and with chlorophyll.

This plant most resembles "Ministar" (unpatented) and differs by having a plainly more rounded flower petal, a spray which is more gathered at the top, and by its resistance to *Fusarium oxysporum.*

We claim:

1. The new and distinct spray carnation cultivar, substantially as herein shown and described, chracterized by the variegated light and dark red appearance of its small blossoms which are produced profusely on long, straight and strong flowering stems; and by its vigorous and upright growth habit, abundant foliage, and resistance to *Fusarium oxysporum.*

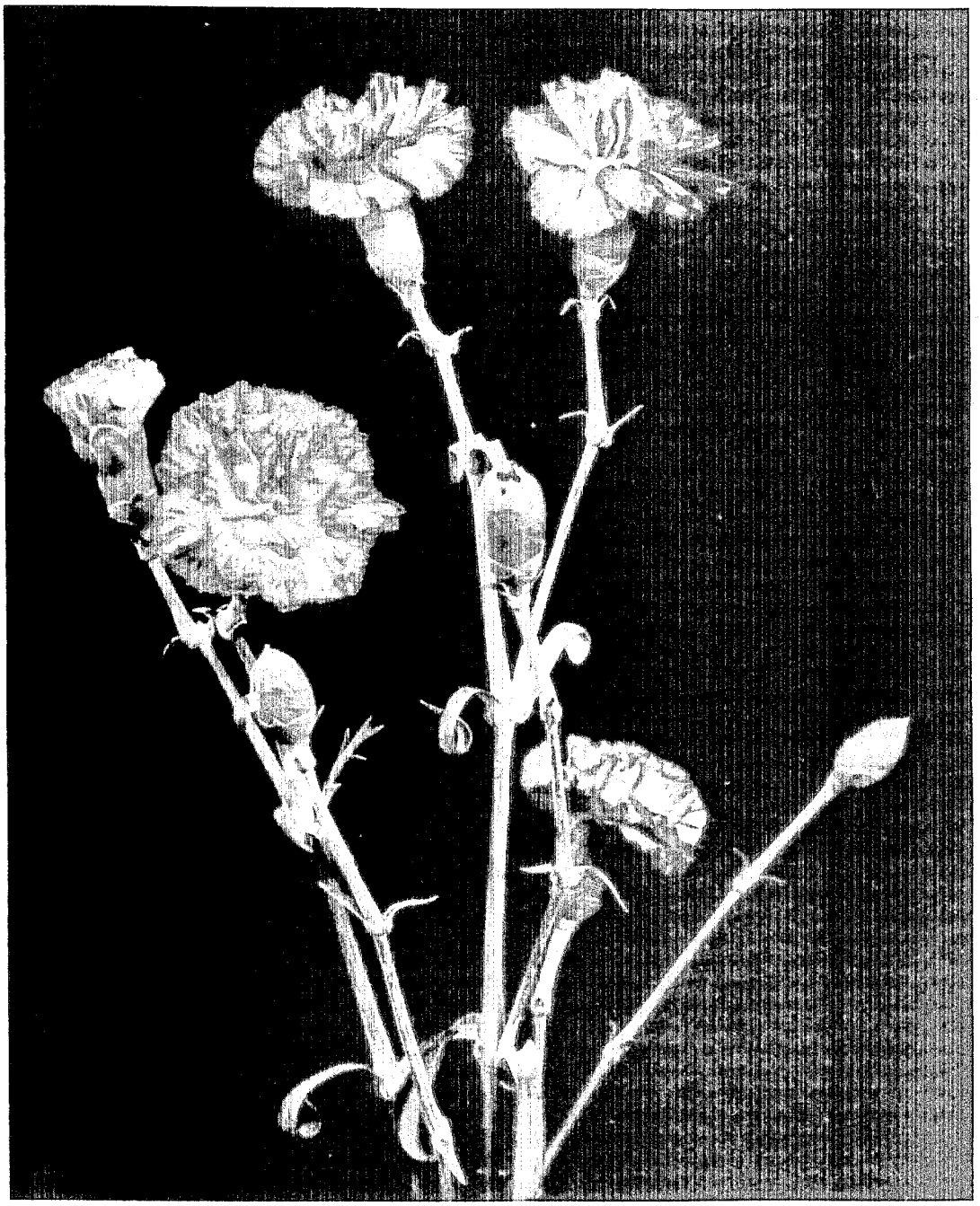

* * * * *